United States Patent
Ellson

(10) Patent No.: US 8,361,418 B2
(45) Date of Patent: Jan. 29, 2013

(54) METHOD FOR STORING FLUID WITH CLOSURE INCLUDING MEMBERS WITH CHANGEABLE RELATIVE POSITIONS AND DEVICE THEREOF

(75) Inventor: Richard N. Ellson, Palo Alto, CA (US)

(73) Assignee: Labcyte Inc., Sunnyvale, CA (US)

( * ) Notice: Subject to any disclaimer, the term of this patent is extended or adjusted under 35 U.S.C. 154(b) by 0 days.

(21) Appl. No.: 13/105,790

(22) Filed: May 11, 2011

(65) Prior Publication Data
US 2011/0277425 A1 Nov. 17, 2011

Related U.S. Application Data

(63) Continuation of application No. 11/698,004, filed on Jan. 24, 2007, now abandoned.

(60) Provisional application No. 60/761,908, filed on Jan. 24, 2006.

(51) Int. Cl.
*G01N 33/00* (2006.01)

(52) U.S. Cl. ........ 422/553; 422/554; 422/560; 422/561; 422/566

(58) Field of Classification Search .................. 422/553, 422/554, 560, 561, 566
See application file for complete search history.

(56) References Cited

U.S. PATENT DOCUMENTS

| | | |
|---|---|---|
| 601,568 A | 3/1898 | Jacoby |
| 1,931,216 A | 10/1933 | Zell |
| 1,983,139 A | 12/1934 | Lovell |
| 2,150,536 A | 3/1939 | Ziehm, Jr. |
| 2,273,247 A | 2/1942 | Barnby et al. |
| 2,279,165 A | 4/1942 | Grace |
| 2,505,641 A | 4/1950 | Howe |
| 2,535,455 A | 12/1950 | Reilly |
| 2,629,764 A | 2/1953 | Wiley |
| 3,139,212 A | 6/1964 | Stallard |
| 3,344,974 A | 10/1967 | Dold |
| 3,795,337 A | 3/1974 | Nozawa et al. |
| 3,800,972 A | 4/1974 | Raymond |
| 3,826,717 A | 7/1974 | Gilbert et al. |
| 3,888,232 A | 6/1975 | Le Brun |
| 3,941,275 A | 3/1976 | Simmons |
| 3,944,102 A | 3/1976 | Grau |
| 3,990,604 A | 11/1976 | Barnett et al. |
| 4,042,143 A | 8/1977 | Biggins |
| 4,090,604 A | 5/1978 | Reifert |
| 4,163,503 A | 8/1979 | McKinnon |
| 4,177,932 A | 12/1979 | Cleevely |
| RE30,326 E | 7/1980 | Van Buren, Jr. |
| 4,391,384 A | 7/1983 | Moore et al. |
| 4,451,693 A | 5/1984 | Vest |

(Continued)

FOREIGN PATENT DOCUMENTS
WO  WO 2005/000469  1/2005

OTHER PUBLICATIONS

Fillers, W.S., "Automated Microplate Sealing and Unsealing with SealTite," a poster found online at http://lab-robotics.org/Presentations/Posters/Poster2038.pdf.

*Primary Examiner* — Sam P Siefke
(74) *Attorney, Agent, or Firm* — Jones Day

(57) ABSTRACT

In a preferred embodiment of the invention, a closure for a container comprises at least two closure members. The relative position of the closure members with respect to each other is altered upon mating of the closure and container. The alteration of the relative position of the closure members may result in one or more of the members approaching the container more closely. The alteration may result in one or more of the members pressing against the container. The pressing may take place in such a way that exit paths for vapor from fluid in the container would require passage through the pressed surfaces.

9 Claims, 9 Drawing Sheets

U.S. PATENT DOCUMENTS

| | | | |
|---|---|---|---|
| 4,494,671 A | 1/1985 | Moore et al. | |
| 4,527,701 A | 7/1985 | Schaubeck | |
| 4,657,867 A | 4/1987 | Guhl et al. | |
| 4,798,706 A | 1/1989 | Brigati | |
| 4,801,040 A | 1/1989 | Kraus | |
| 4,883,194 A | 11/1989 | Fernandes | |
| 4,971,774 A | 11/1990 | Schwanke et al. | |
| 4,997,100 A | 3/1991 | Dudek | |
| 5,020,681 A | 6/1991 | Kusz | |
| 5,168,995 A | 12/1992 | German | |
| 5,181,626 A | 1/1993 | Daenen et al. | |
| 5,240,113 A | 8/1993 | Gibilisco | |
| 5,360,270 A | 11/1994 | Appeldom et al. | |
| 5,368,186 A | 11/1994 | Yeh | |
| 5,402,885 A | 4/1995 | Cook et al. | |
| 5,411,157 A | 5/1995 | King et al. | |
| 5,454,479 A | 10/1995 | Kraus | |
| 5,459,300 A | 10/1995 | Kasman | |
| 5,487,484 A | 1/1996 | Bonniau et al. | |
| 5,505,324 A | 4/1996 | Danico | |
| 5,513,769 A | 5/1996 | De Baets | |
| 5,562,222 A | 10/1996 | Jordan et al. | |
| 5,587,321 A | 12/1996 | Smith et al. | |
| 5,667,092 A | 9/1997 | Julius et al. | |
| 5,682,910 A | 11/1997 | Kizawa et al. | |
| 5,691,878 A | 11/1997 | Ahn et al. | |
| 5,702,133 A | 12/1997 | Pavur et al. | |
| 5,741,463 A | 4/1998 | Sanadi | |
| 5,772,967 A | 6/1998 | Wannlund et al. | |
| 5,852,854 A | 12/1998 | Pierrot et al. | |
| 5,863,792 A | 1/1999 | Tyndorf et al. | |
| 5,893,480 A | 4/1999 | Dore et al. | |
| 5,988,392 A | 11/1999 | Hosoi | |
| 6,015,534 A | 1/2000 | Atwood | |
| 6,258,325 B1 | 7/2001 | Sanadi | |
| 6,394,300 B1 | 5/2002 | Bosy | |
| 6,426,050 B1 | 7/2002 | Pham et al. | |
| 6,426,215 B1 | 7/2002 | Sandell | |
| 6,436,351 B1 | 8/2002 | Gubernator et al. | |
| 6,451,261 B1 | 9/2002 | Bodner et al. | |
| 6,486,401 B1 | 11/2002 | Warhurst et al. | |
| 6,534,014 B1 | 3/2003 | Mainquist et al. | |
| 6,565,813 B1 | 5/2003 | Garyantes | |
| 6,622,864 B1 * | 9/2003 | Debbs et al. | 206/438 |
| 6,815,199 B1 | 11/2004 | Kubota | |
| 6,832,686 B2 | 12/2004 | Donegan | |
| 6,875,604 B2 | 4/2005 | Shin et al. | |
| 6,896,848 B1 | 5/2005 | Warhurst et al. | |
| 6,939,516 B2 | 9/2005 | Hall et al. | |
| 6,966,153 B2 | 11/2005 | Panetta et al. | |
| 7,036,678 B2 | 5/2006 | Eiskant et al. | |
| 7,081,600 B2 | 7/2006 | Brown et al. | |
| 7,169,355 B1 | 1/2007 | Shin et al. | |
| 7,267,246 B2 | 9/2007 | Eiskant et al. | |
| 7,429,479 B2 | 9/2008 | Harding | |
| 7,455,192 B2 | 11/2008 | Siragusa | |
| 7,460,223 B2 | 12/2008 | Harding | |
| 7,500,578 B1 | 3/2009 | McKinnon, Jr. | |
| 7,854,343 B2 | 12/2010 | Ellson et al. | |
| 2001/0011620 A1 | 8/2001 | Tiramani et al. | |
| 2001/0049149 A1 | 12/2001 | Kennedy et al. | |
| 2002/0006361 A1 | 1/2002 | Sanadi | |
| 2002/0039545 A1 | 4/2002 | Hall et al. | |
| 2002/0190070 A1 | 12/2002 | Panetta et al. | |
| 2003/0108450 A1 | 6/2003 | Mainquist et al. | |
| 2003/0124549 A1 | 7/2003 | Beutler et al. | |
| 2003/0150257 A1 | 8/2003 | Mutz et al. | |
| 2004/0018615 A1 | 1/2004 | Garyantes | |
| 2005/0019224 A1 | 1/2005 | Pechter et al. | |
| 2005/0019225 A1 | 1/2005 | Sanadi | |
| 2005/0048575 A1 | 3/2005 | Coassin et al. | |
| 2005/0226787 A1 | 10/2005 | Shanler | |
| 2006/0024204 A1 | 2/2006 | Oldenburg | |
| 2006/0201948 A1 | 9/2006 | Ellson et al. | |

* cited by examiner

US 8,361,418 B2

METHOD FOR STORING FLUID WITH CLOSURE INCLUDING MEMBERS WITH CHANGEABLE RELATIVE POSITIONS AND DEVICE THEREOF

CROSS-REFERENCE TO RELATED APPLICATIONS

This application is a continuation of U.S. patent application Ser. No. 11/698,004, filed Jan. 24, 2007, which claims priority to U.S. Provisional Patent Application No. 60/761,908, both of which are incorporated by reference in their entirety.

TECHNICAL FIELD

This invention relates generally to containers for fluids, and in particular to containers for small quantities of fluid used in chemical and biomedical research and development.

BACKGROUND

In chemical and biomedical research and development, it is common to manipulate large numbers (e.g., thousands) of fluid containers which must be readily and automatably opened and closed, and yet must also be stored for months or years. The need to open and close the containers readily tends to induce the use of relatively poorly sealed containers, whereas the desire to store the containers for months or years tends to make it desirable to achieve tight sealing, for example to avoid evaporation loss and contamination from the outside.

The fluid containers used in chemical and biomedical research are subject to substantial chemical compatibility constraints, for example that they should not be made of materials which would be attacked by the solvents which they are designed to hold. Such constraints will also apply to the closures of such fluid containers. Adhesives are generally not preferred for closure of such fluid containers because of concerns about contamination and nonuniformity arising from adhesive residue left over from one closure to the next. Adhesives are nonetheless in widespread use.

Examples of fluid containers widely used in chemical and biomedical research and development are well plates and micro tubes. Well plates are commonly used which have 96, 384, and 1536 wells, although other numbers of wells are also in use. The dimensions and other characteristics of well plates have been standardized by the Society for Biomolecular Screening. A common size of well plate is 127.76 by 85.48 by 14.35 mm. Well plates are commonly designed to be stacked on top of each other in storage. Microtubes are commonly used in racks of 96 or 384. These racks of microtubes conform to dimensions similar to the length and width of well plates so they can be handled by similar robotic and automation equipment.

For well plates, a wide variety of lids have been developed. An example of a well plate lid of the prior art is described in U.S. Patent Application Publication No. 2003/0108450. That well plate lid uses the weight of the lid to provide the force which holds the lid to the well plate. The lid is stated to weigh 400 g preferably. A compliant sealing member, preferably of silicone rubber, forms part of the lid and is pressed against the well plate.

A commercially available lid for well plates is the SealTite lid from TekCel, Inc. (Hopkinton, Mass.). The SealTite lid has a metal spring/clamp structure to form a better seal than would be possible if the weight of the lid were the only force holding the lid to the well plate. The use of force as provided, for example, by a spring/clamp may give rise to difficulties in automation of the handling of well plates with lids. See in this regard the TekCel poster at http://lab-robotics.org/Presentations/Posters/Poster2038.pdf.

There have also been efforts in the art to adapt to evaporation losses. In particular, in some cases the outer wells of a well plate are not used to hold fluids of interest but instead are filled with a volume of the solvent in which those fluids are stored. This solvent in the outer wells has been observed to reduce the rate at which the solvent in the inner wells evaporates. The outer wells are sometimes referred to as "moat wells" when so used.

An alternative means to adapt to evaporation losses is to periodically audit the fluid levels in the reservoirs of the container and to add solvent to those reservoirs as needed. United States Patent Application Publication No. 2003/0150257 describes a convenient automatable way of carrying out the auditing by means of focused acoustic energy.

Cost considerations make it preferable for the containers and their closures to be manufactured by means of molding or similarly economical processes, with limited or no machining. Typical molding processes such as injection molding result in different reservoirs within a container, such as wells in a well plate, being different from each other. For example, there may be a small overall bending or "bow" across a well plate. Such bow is expected, for example, when polymer is injected into the mold at a single point—the "gate"—which is located in or near the center of a substantially flat part such as a well plate. Such processes may also result in there being dimensional differences between different supposedly identical containers or closures manufactured from the same molds or molds intended to be identical. In addition, because containers and their closures may be manufactured separately, by different companies, there may be dimensional mismatches in both containers and closures which result in imperfections in intended mating of containers and closures.

It is often desired to maintain well plates for periods of months. In such situations, it is desired to be certain that the well plates can last for a known time without need for inspection or replenishment. If even only one well of the well plate loses solvent too quickly, this desirable certainty is not achieved.

There is therefore a need in the art to adapt to the evaporation losses caused by less than perfect seals which are used in order to facilitate the automated opening and closing of containers which hold small quantities of fluid.

SUMMARY OF THE INVENTION

In a preferred embodiment of the invention, a closure for a container comprises at least two closure members. The relative position of the closure members with respect to each other is altered upon mating of the closure and container.

The alteration of the relative position of the closure members may result in one or more of the members approaching the container more closely. The alteration may result in one or more of the members pressing against the container. The pressing may take place in such a way that exit paths for vapor from fluid in the container would require passage through the pressed surfaces.

DRAWINGS

In FIG. 1A the cross section is in a vertical plane whereas in FIG. 1B the cross section is in a horizontal plane.

In FIG. 6B the projection 10 has rounded corners.

DETAILED DESCRIPTION OF EMBODIMENTS OF THE INVENTION

Figure 1A:
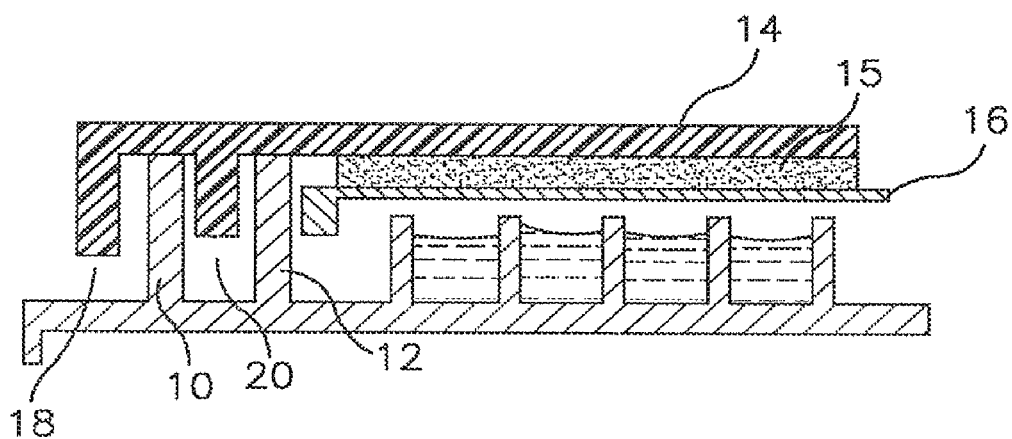
FIGS. 1A-1B depict in schematic partial cross section a container and a closure of the invention as the closure is brought into contact with the container.

Before describing the present invention in detail, it is to be understood that this invention is not limited to specific fluids, containers, or device structures, as such may vary. It is also to be understood that the terminology used herein is for the purpose of describing particular embodiments only, and is not intended to be limiting.

As used in this specification and the appended claims, the singular forms "a," "an," and "the" include both singular and plural referents unless the context clearly dictates otherwise. Thus, for example, reference to "a reservoir" includes a plurality of reservoirs as well as a single reservoir, reference to "a droplet" includes a plurality of droplets as well as single droplet, and the like.

In describing and claiming the present invention, the following terminology will be used in accordance with the definitions set out below.

The term "fluid" as used herein refers to matter that is nonsolid, or at least partially gaseous and/or liquid, but not entirely gaseous. A fluid may contain a solid that is minimally, partially, or fully solvated, dispersed, or suspended. Examples of fluids include, without limitation, aqueous liquids (including water per se and salt water) and nonaqueous liquids such as organic solvents and the like. As used herein, the term "fluid" is not synonymous with the term "ink" in that an ink must contain a colorant and may not be gaseous.

"Optional" or "optionally" means that the subsequently described circumstance may or may not occur, so that the description includes instances where the circumstance occurs and instances where it does not.

The term "reservoir" as used herein refers to a receptacle or chamber for containing a fluid. A reservoir may also be a volume of a member within which a fluid is constrained or held.

The term "closure" as used herein refers to a member used to close a container for fluids. It thus encompasses for example lids, stoppers, and caps. A container may be closed with one closure or, in some cases, with multiple closures. Closures normally meet with containers at respective surfaces on each member. The mechanical match of the closure and container at the surfaces where they meet may not be perfect, so that some exchange of vapor between the inside and outside of the container may be possible even with closures in place.

In a preferred embodiment of the invention, a closure for a container comprises at least two closure members. The relative position of the closure members with respect to each other is altered upon mating of the closure and container.

The alteration of the relative position of the closure members may result in one or more of the members approaching the container more closely. The alteration may result in one or more of the members pressing against the container. The pressing may take place in such a way that exit paths for vapor from fluid in the container would require passage through the pressed surfaces.

A motivation for having closure members press against the container is that, all else being equal, a seal formed by such pressure will be tighter than a seal formed without such pressure.

In many cases the relative motion of the members of the closure is achieved by connecting them in such a way that relative motion is enabled. This can be achieved by an elastic component, through the flexure of a connecting element, or by having the components interlocked with a loose fit.

When closure members press against the container, the force is preferably generated by interaction of the container and the closure, such as through the process of putting the closure on the container. However, the force could be generated through external means such as magnets.

The relative motion of the closure members may be designed such that two members press against the container in directions which are at an angle to each other. This angle may be 90 degrees or greater. In certain embodiments the angle may be approximately 180 degrees, so that two members press against the container in directions which are approximately opposite to each other.

Commonly, the places at which the container and closure meet when the container is closed are close to a horizontal plane. The closure in normal use commonly lies on top of the container. In that way, the force of gravity helps the closure remain affixed to the container.

The container may be designed so that it has approximately vertical projections which meet the closure. For example, a closure which is roughly flat and rectangular in form, as for example a well plate, may have two concentric vertical projections surrounding its outer edge, and the closure may be designed to meet one or both of the vertical projections.

Figure 1B:
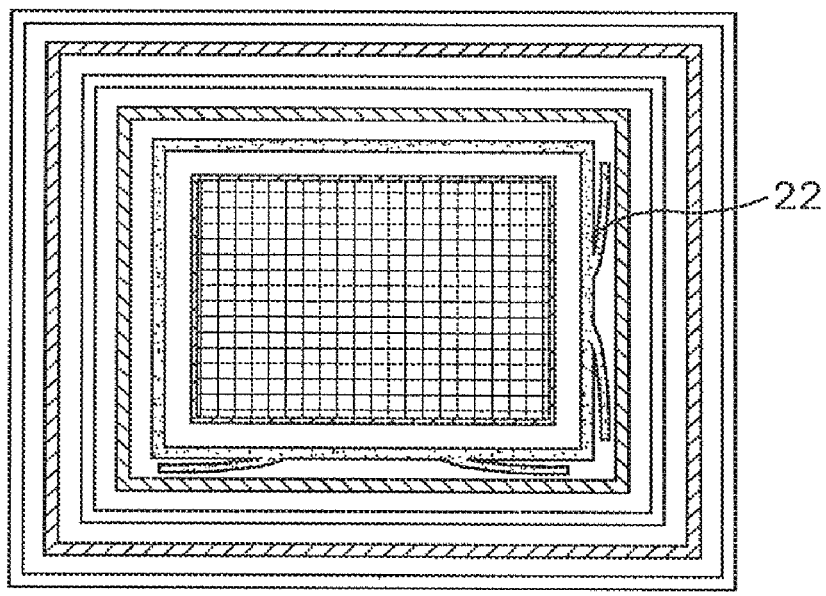

FIGS. 1A-1B depict an exemplary embodiment of the invention in which the container is a well plate and the closure is a lid for the well plate. The top portion of the figure depicts a vertical cross section through part of the container and closure. The bottom portion depicts a horizontal cross section through the container and closure. The container has two vertical projections 10 and 12 around its circumference. The closure has an upper and a lower member 14 and 16. In between the upper and lower members there is a reservoir 15 for liquid. The upper member has two vertical projections 18 and 20 around its circumference. The lower member is designed to be on the inside of both vertical projections. An elastic component causes the lower member to press against the inner projection on the plate. In FIGS. 1A-1B, this elastic component is show as being composed of four parts 22 attached to two sides of the lower closure member.

Figure 2A:
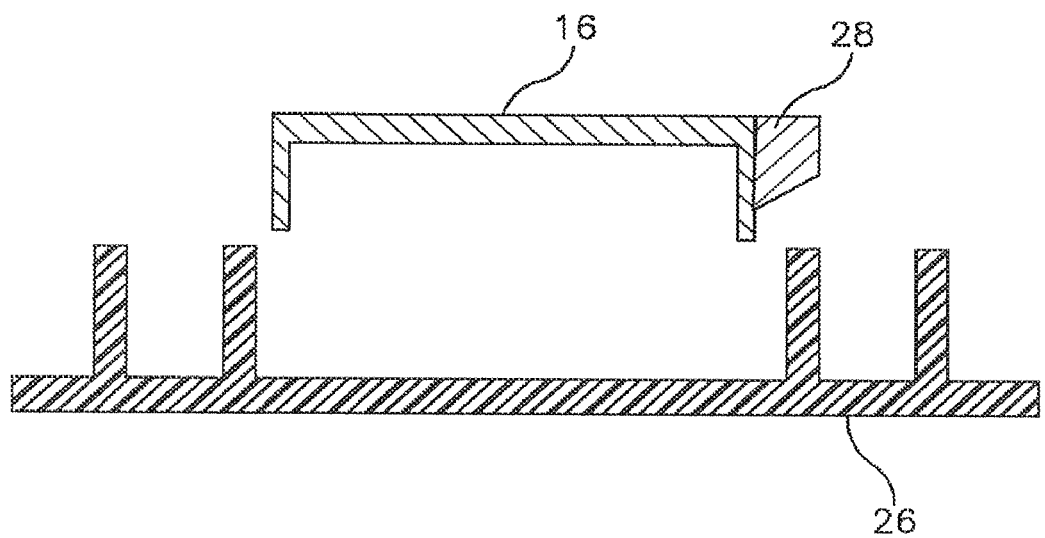
FIGS. 2A-2B depict schematically a possible arrangement for the elastic component of one portion of the closure of the invention.
Figure 2B:
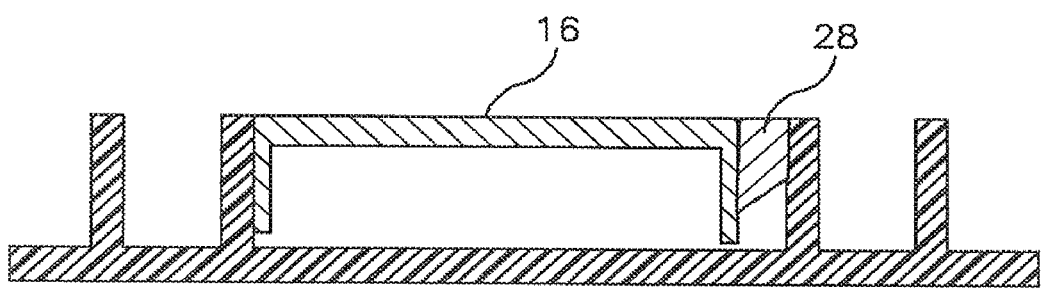

FIGS. 2A-2B depict schematically an exemplary construction for the elastic component in the context of the embodiment of FIGS. 1A-1B. Like the upper part of FIGS. 1A-1B, this figure is a vertical cross section through the container and closure. For simplicity, this figure depicts only the lower closure member 16 and a portion of the elastic component which acts upon that lower member. In the upper part of the figure, we see the lower closure member 16 prior to contact between closure and container 26. The elastic component, which comprises one or more flexible members 28 attached at one end to the lower closure member as in FIGS. 1A-1B, is depicted here to the right of the closure in the figure. As the lower closure member 16 is lowered into position, the elastic component 28 responds to the presence of the container and bends, generating a force that sends the lower closure member 16 leftwards. The pressure forces the lower closure member against the left wall of the inner projection of the container.

Figure 3A:
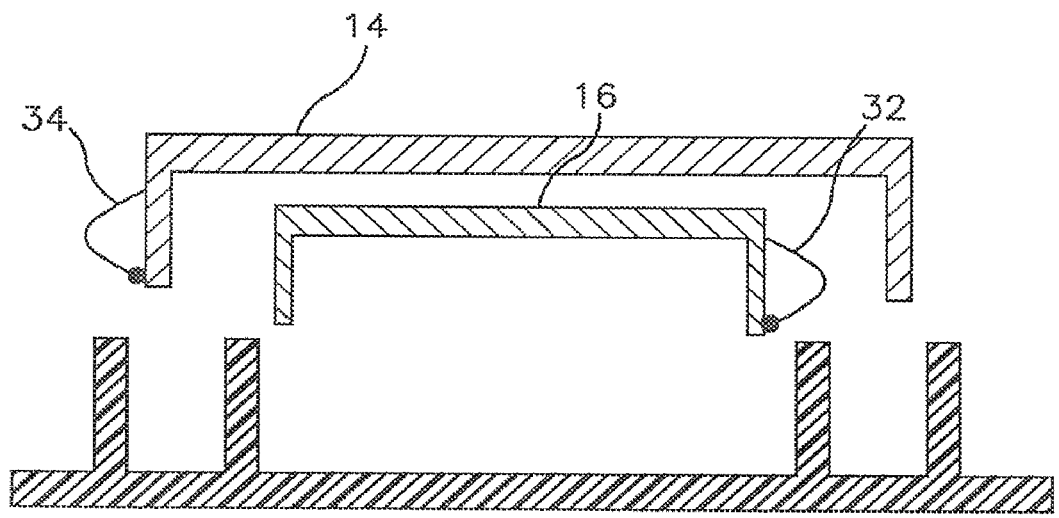
FIGS. 3A-3B depict schematically a possible arrangement for the elastic component for both the upper and lower members of the closure of the invention.
Figure 3B:
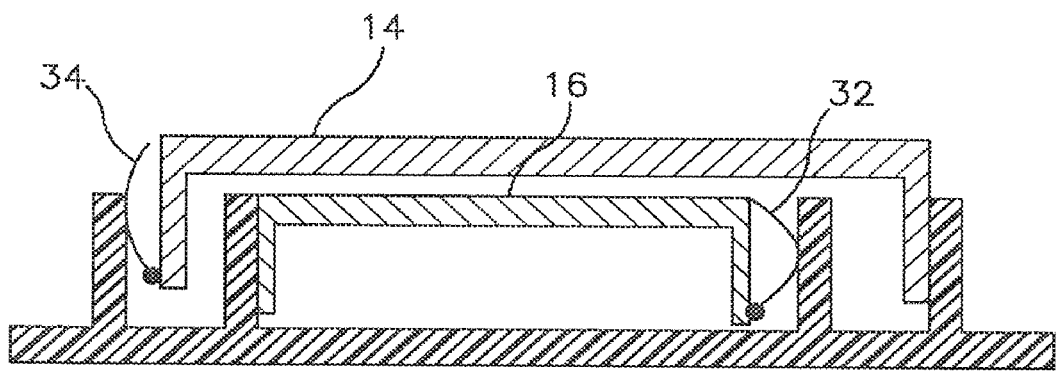

In FIGS. 3A-3B we see a schematic cross-section of a closure of the invention depicting both the upper and lower members of the closure 14 and 16. In this figure, the upper and lower closure members both have portions 32 and 34 of an elastic component attached. The elastic component is of a somewhat different design than that shown in FIGS. 1A-1B and 2A-2B, being attached towards the bottom of the closure member wall and extending upward. For the upper closure member 14, the corresponding portion 34 of the elastic component is shown attached at the left hand side, while the lower member 16 has its portion 32 of the elastic component depicted as being attached on the right hand side. Again, as in FIGS. 2A-2B, when the upper and lower members of the closure are lowered onto the container, the elastic component acts upon them to the right and to the left respectively. Thus, the upper member presses against the outer projection of the container while the lower member presses against the inner projection.

Figure 4:
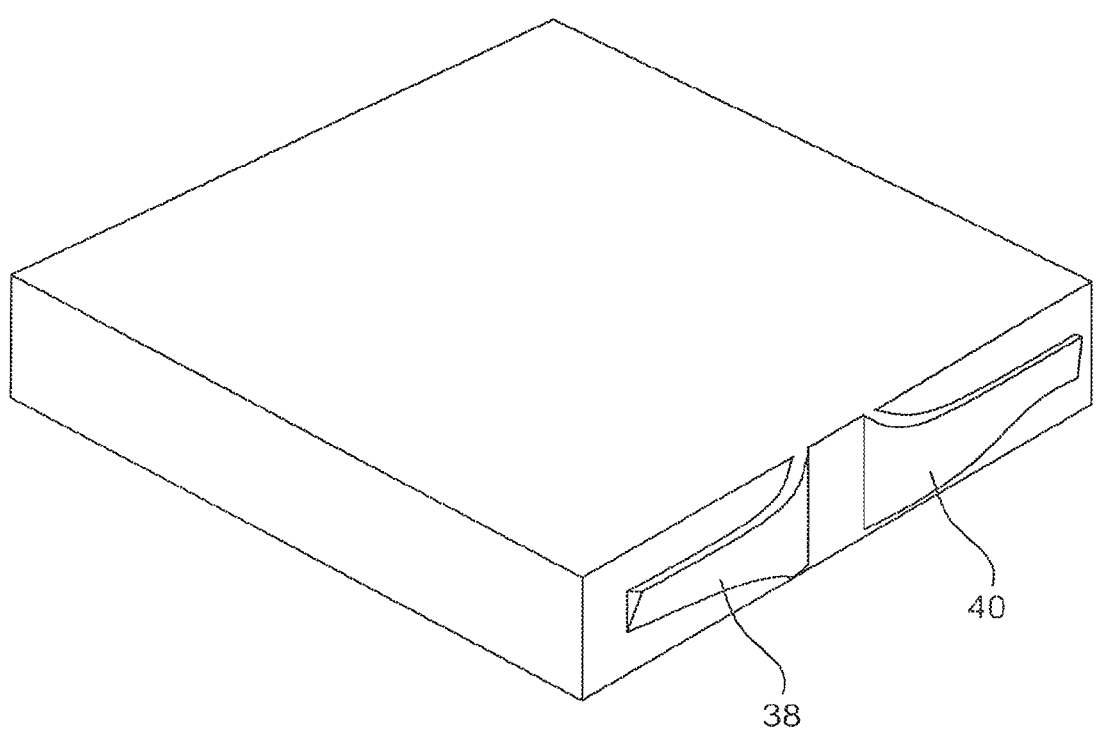
FIG. 4 depicts schematically an arrangement of spring-like structures on one sides of one of the members of a closure of the invention.

FIG. 4 provides further detail on an elastic component of the kind depicted in FIGS. 1A-1B and 2A-2B. The elastic component has two spring-like parts 38 and 40 which project outwards from a side of a closure member. Each of the spring-like pieces that make up the elastic component is tapered and also has a tapered cross-section. The form of the pieces is thus somewhat like that of a wing. While FIG. 4 shows the spring-like pieces 38 and 40 as having a sharp bottom edge, the bottom edge may also be rounded or blunt, and the tapering of both the overall shape and of the cross-section may be more or less gradual. In this embodiment it is intended that the downward force of placing the closure on the container will first apply force between the finger and shoulder of the spring-like pieces 38 and 40 to press them closer into the body. The exact point at which the spring-like pieces will make contact with the container depends on design details as well as deviations from nominal dimensions and misalignment of closure and container in the insertion process. The intent, however, is that as contact is made the spring-like pieces 38 and 40 are forced towards the main portion of the closure member, exerting a force on it.

Figure 5:
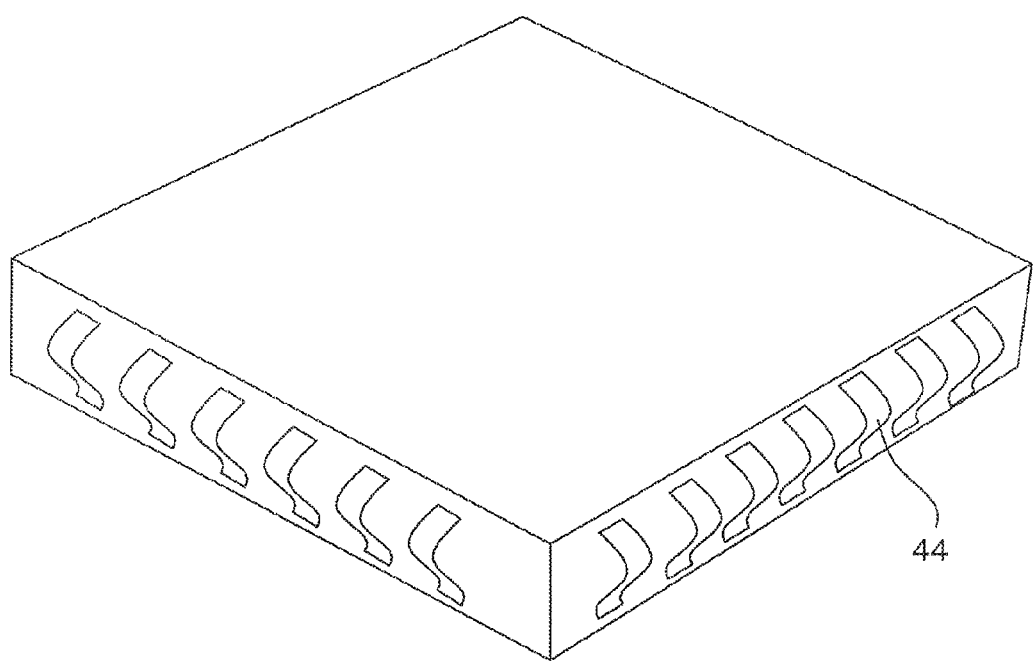
FIG. 5 depicts schematically an arrangement of spring-like structures on two sides of one of the members of a closure of the invention.

It is also possible in the embodiments of FIGS. 2A-2B and 3A-3B to use more than one spring-like structure on each side of the inner and outer members. For example, we could have three or five or ten spring-like structures attached to one side of the lower member. In addition, we could have spring-like structures attached to two adjacent (non-opposite) sides of the lower member. This is shown in FIG. 5, which depicts schematically a member of a closure of the invention with a number of spring-like structures such as 44 on each of two adjacent sides. That would result in the lower member pressing against a corner of the container projection and thus making a better, more sealing contact against two of the walls of the container projection. The same multiplicity of spring-like structures is possible for the upper member.

If the spring-like structures of the upper member press against a corner of the outer container projection opposite to the corner of the inner container projection against which the lower member presses, then the interior of the inner container projection is almost entirely surrounded by a superior, more sealing contact on all four sides. This may be seen in FIGS. 6A-6B, a bottom view where the shaded rectangles depict the positions of the upper closure member 14 and lower closure member 16 relative to the projections 10 and 12 on the container in the embodiment of FIGS. 3A-3B. As may be seen, a molecule of fluid from the container escaping by diffusion towards the outside will find its path blocked by the superior, pressure-assisted seals on the right and bottom (shown as thicker lines). It will therefore tend to move outward through the sides of the inner projection 12 which are not blocked by such seals (shown as thinner lines). However, if it moves outward through those sides, it will tend to be blocked by the superior, pressure-assisted seals on outer projection 10 depicted at the left and top (also shown as thicker lines).

Figure 6A:
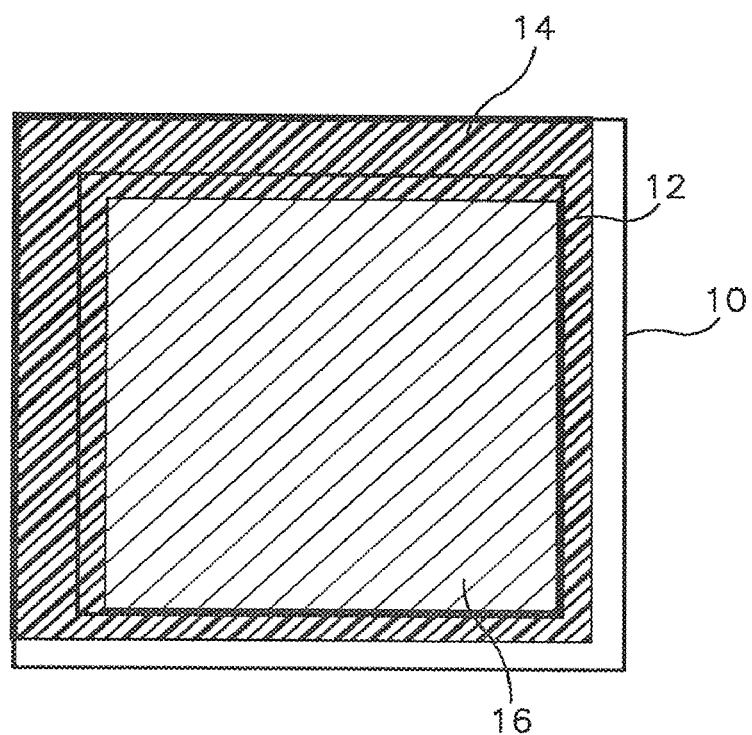
FIGS. 6A-6B depict schematically the positions of the upper and lower members of a closure of the invention relative to projections in the container.
Figure 6B:
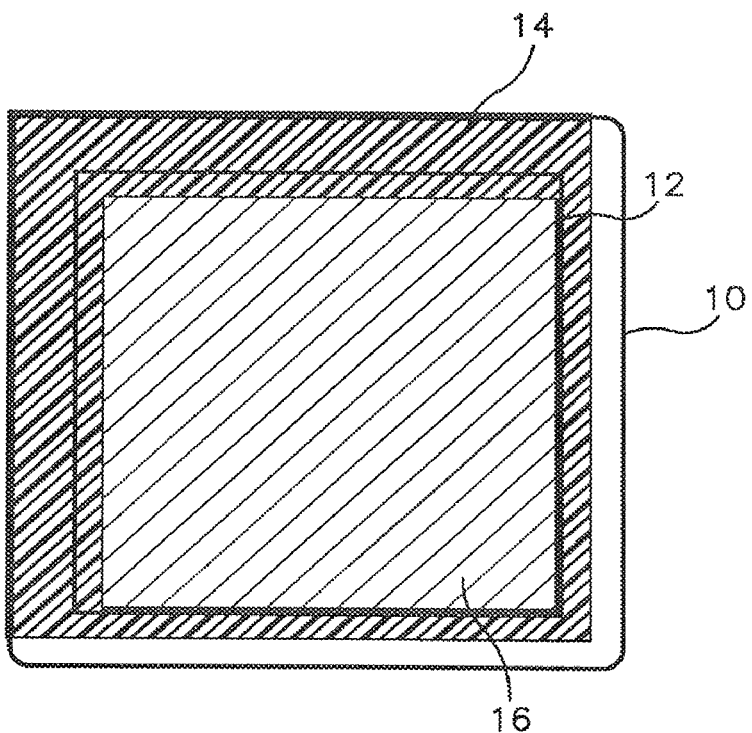
Figure 7A:
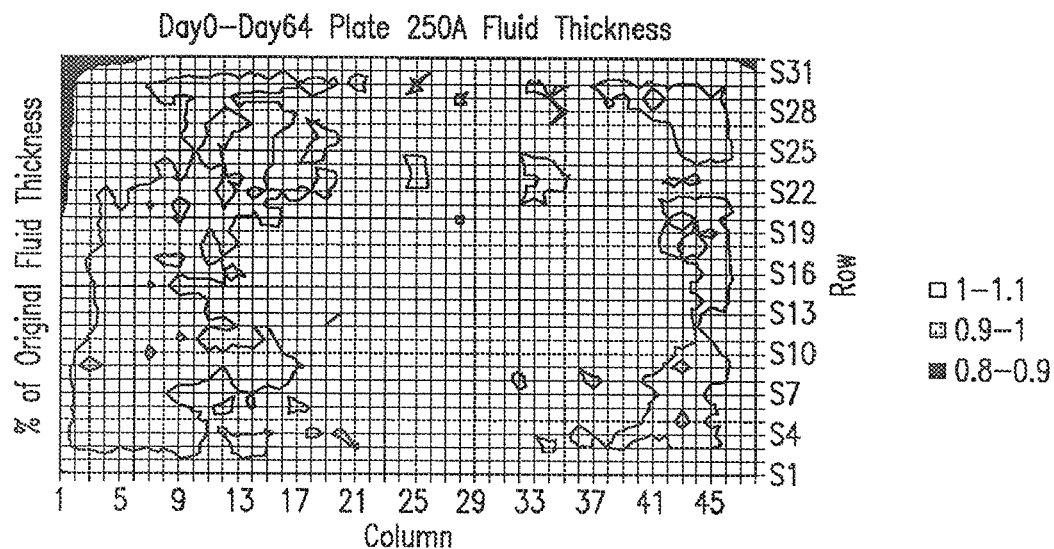
FIGS. 7A-7F depict the results of an experiment in which four closures which press against projections on a well plate are compared to two control closures.
Figure 7B:
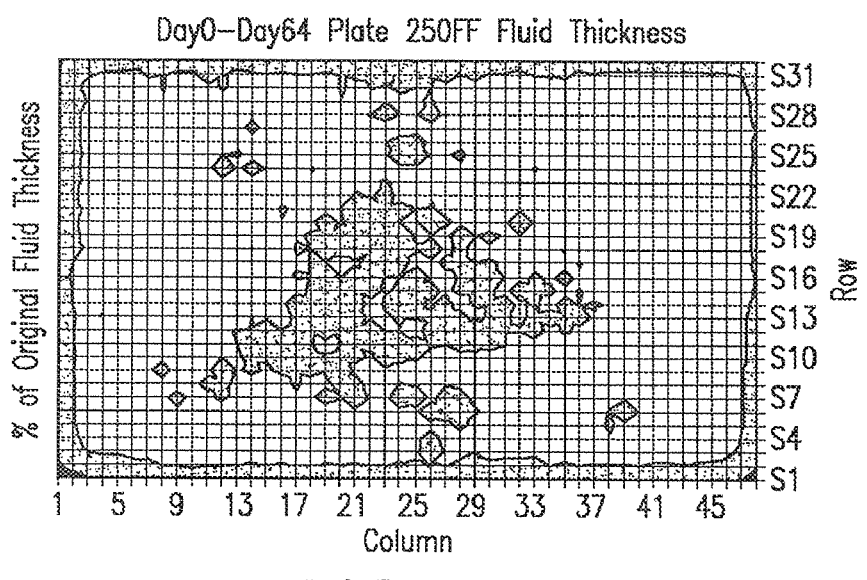
Figure 7C:
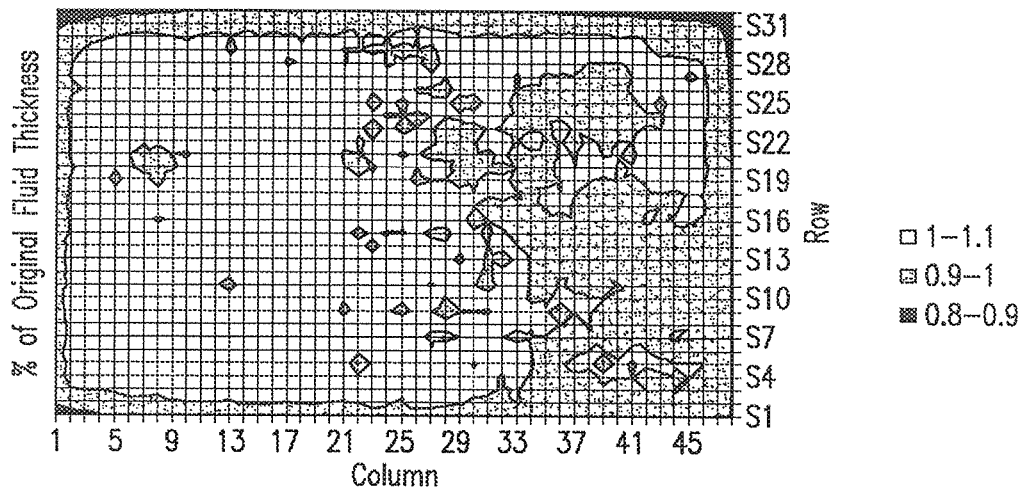
Figure 7D:
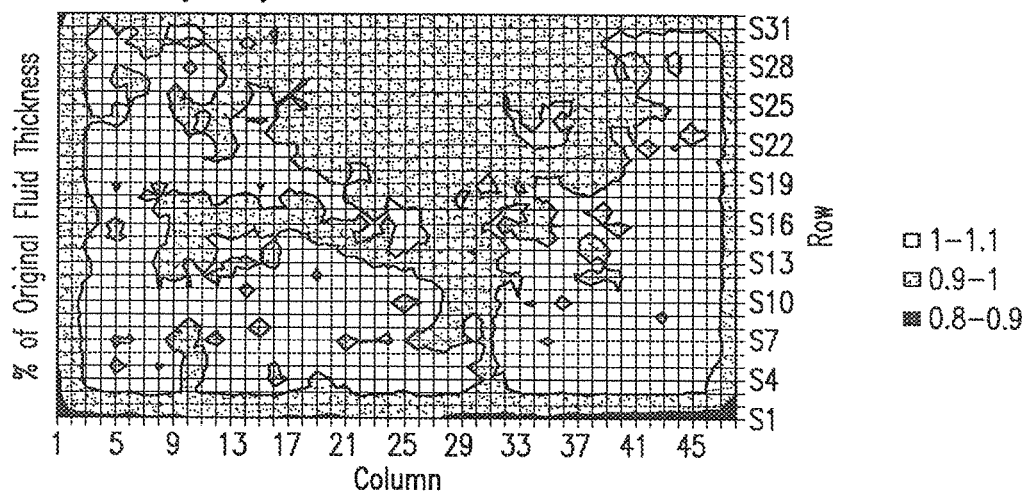
Figure 7E:
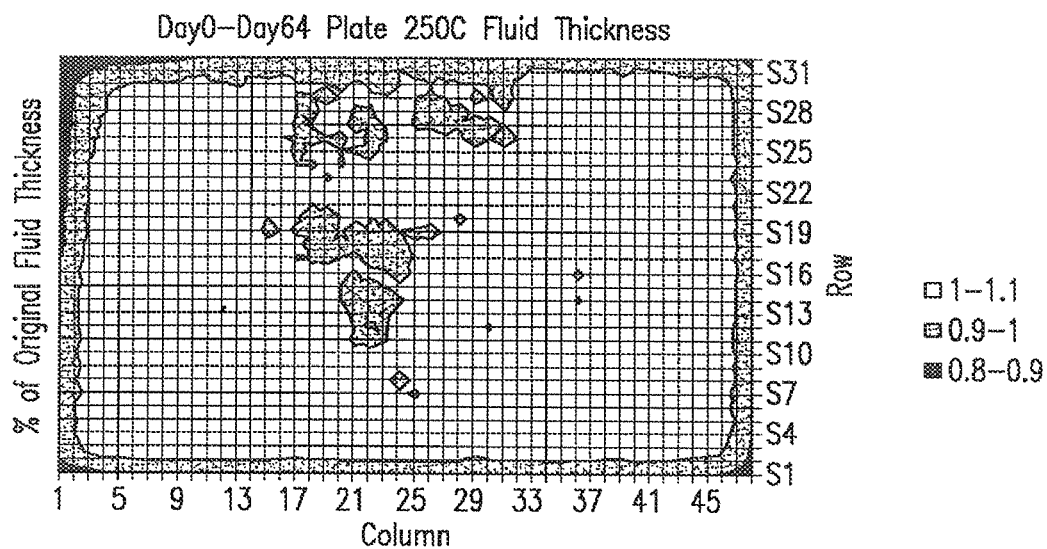
Figure 7F:
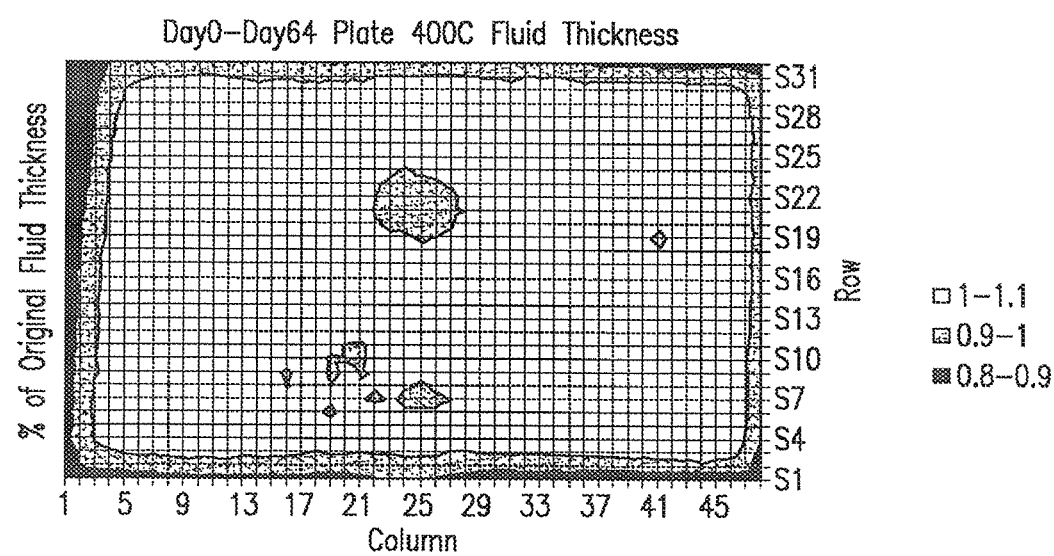

In situations where the fluid in the container is hygroscopic and thus tends to trap water molecules which diffuse inward, the arrangement depicted in FIGS. 6A-6B will also tend to limit the inward diffusion of water.

In FIGS. 3A-3B for simplicity the upper and lower members of the closure are not depicted as being connected. It would be possible for the two members of the closure to be separate, although that would have the disadvantage that they would have to be removed in two operations. Alternatively, it is possible to have the two members of the closure be connected provided the connection between them has sufficient elasticity to allow them to be pushed apart as required for them to press against the closure as discussed above.

It is desired in certain embodiments that the closure be easily put into contact with the container and removed from contact with the container, for example by a robot arm or similar automated piece of machinery. Commonly, when this is carried out, the container is held firmly while the robot arm also presses firmly against the closure. When the closure needs to be brought into contact with the container, the robot arm brings the closure into a suitable, calculated position atop the container and then presses down with moderate force. The position into which the closure is put may need to be determined based on the position of the container, which may for example be sensed by some type of sensor.

In U.S. patent application Ser. No. 11/077,630, closures containing reservoirs for solvent are described. Such reservoirs are conveniently employed in the closures of the present invention. While many of the techniques described in the 11/077,630 application are usable with the closures of the present invention, a particularly attractive possibility is for a reservoir for solvent to be attached to the top of the lower closure or bottom of the upper closure. The solvent reservoir could, for example, be made of a substance which absorbs and holds the solvent.

In application 11/077,630 referred to above there is also a discussion of so-called "labyrinth seals." In general, it is desirable for the closures of the invention to be so arranged as to make a labyrinth seal which serves to prevent the outward diffusion of volatilizing solvent and the inward diffusion of water and of other undesirable vapor into the container.

The materials of which the closure could be made are dependent on the types of fluids which the reservoir contains. The two members of the closure may be made, for example, of polymers widely used for the manufacture of well plates as described in the literature. Fluids where DMSO by itself or DMSO and water are solvents are of particular interest in chemical and biomedical research. Materials for closures which are compatible with DMSO include cyclic olefin copolymers (COC), polyethylene (PE), polypropylene (PP), ethylene-propylene rubber (EPR) and polytetrafluoroethylene (PTFE). COC is made by Ticona Engineering Polymers (Summit, N.J.), which is part of Celanese Corporation, and goes by the trade name Topas. One preferred Topas resin is 8007.

The elastic component may be made of a suitable polymer having the appropriate elasticity, or alternatively for example of a metallic alloy such as steel. It may be desirable that the elastic component be made of a polymer which can conveniently be welded ultrasonically to the closure members. It may alternatively be desirable that the elastic component be made integral to the closure members and that the elastic component be fabricated in the same molding process that serves to fabricate the closure members. It is believed that an elastic component as depicted in FIG. 4 can be fabricated in the same molding process as the closure member to which it is attached.

Instead of two members it would be possible to practice this invention with three, four, or more closure members, each pressing against a particular zone in the container. If the container included, for example, three rather than two concentric projections around its circumference, there could be value in having a third closure member lying above the upper member in an embodiment analogous to FIGS. 3A-3B, pressing against the outermost of the concentric projections in the container.

It is generally desired that closure members be dimensioned for convenient insertion into the corresponding portions of the container with which they are intended to mate, leaving as small a gap as is compatible with successful insertion taking into account the dimensional variation encountered both in the closure members and in the containers themselves, as well as the accuracy of positioning achievable with available robots. In general, each of these tolerances may be expected to be on the order of a few tenths of a millimeter, so that it is generally desired that the gap between a closure member and the portion of the container with which it is intended to mate be less than 2 mm, preferably less than 1.5 mm or less than 1 mm, more preferably less than 0.8 mm or less than 0.4 mm or less than 0.25 mm.

In the figures of this application the projections of the closures and containers have been depicted as being vertical. While it is preferred that these projections be approximately vertical, it is advantageous that such projections be 1, 2, 3, or more degrees away from the vertical. This facilitates their extraction from the mold during manufacture if they are made by a molding process. The desired angle will vary with the material, molding conditions and other factors know to those of skill in the art. This deviation from being precisely vertical also facilitates their coming into contact as the closure is lowered, as depicted for example in FIGS. 3A-3B, lower part. When a closure is designed to work with a particular container, it is desirable that the projections in the closure which will press against projections on the container be designed to have an angle of deviation from the vertical which matches the angle of deviation of the projections in the container.

As will be appreciated by those of skill in the art, gravitational force assists in the maintenance of the seals in closures of the invention where their projections which meet corresponding projections in the container have a deviation from the vertical. While it is desirable from a simplicity and cost standpoint not to add artificial weight to the closures of the invention, it would be possible to do so if that were seen as valuable for improving the quality of the seal due to the additional force which gravity would exert in that case.

In FIGS. 2A-2B, 3A-3B, 4, and 5 for simplicity the elastic component of the closures has been depicted as lying on the outside walls of rectangular members. It will be appreciated that if a robot or other such machine, or a human hand, were to pick up closure members so designed (e.g., as depicted in FIG. 5) it would press against the elastic component. For this reason it may be better in some cases to have at least the outer closure member have an overhang or projection at the top at which it can be gripped.

It is to be understood that while the invention has been described in conjunction with the preferred specific embodiments thereof, that the foregoing description and the examples that follow are intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

EXAMPLE

Well plates containing DMSO were tested over a 64-day period. Each well plate had two concentric projections around its circumference. Two well plates, 400C and 250C, had a closure which contained a reservoir for DMSO but did not have any elastic component causing the closure to press against the well plate. Four well plates were provided with a single elastic component causing the closure to press towards a corner of the projections. Two of these, 400A and 250A, were connected to an elastic component causing the closure to press towards the lower right corner; two others, 400FF and 250FF, were connected to an elastic component causing the closure to press towards the upper left corner. The well plates denoted by numbers beginning with 400 had closures designed to leave a 400 micrometer gap between a projection on the well plate and the closest projection on the closure; those denoted by numbers beginning with 250 had closures designed to leave a 250 micrometer gap between a projection on the well plate and the closest projection on the closure. No screws, clips, adhesives, or any other means besides the weight of the closure and the elastic components were used to maintain the seal between the closures and the well plates.

The results obtained are depicted in FIGS. 7A-7F. In the figures, the black color denotes wells within the well plate where the fluid content fell to less than 90% of the original fluid content during the 64-day test period. It is desired that there be no wells of this type in the well plate. As may be seen the closures which press against a corner achieved generally a smaller number of wells of this type and in general no wells of this type in the quadrant towards which they pressed. This suggests that a closure of the type described above in connection with FIGS. 3A-3B will achieve no wells with more than 10% DMSO loss over two months.

Similar improvements in the lid performance would be expected for protecting other solvents in the container when covered by the closure containing a reservoirs of the solvent. For example, to preserve aqueous solutions in the container, the lid may be filled with water. Compared to DMSO, water is lighter and more volatile. It would be expected to both evaporate more rapidly and have a faster rate of diffusion. Hence, the time scales for the process would be much faster, measuring in days rather than months. Performance of a closure of this type with water would be expected to achieve no wells with more than 10% water loss over a period of three days.

I claim:

1. A method for storing one or more fluid samples, the method comprising:
   storing one or more fluid samples in one or more reservoirs of a container, the container including a first sidewall and a second sidewall, the second sidewall surrounding the first sidewall, the first sidewall surrounding the one or more reservoirs;
   covering the container with a closure, the closure including a first closure component and a second closure component, the first closure component including a first top component, a first side component and a first elastic component attached to the first side component, the second closure component including a second top component, a second side component and a second elastic component attached to the second side component, the first top component and the second top component being in different positions; and
   keeping the container covered with the closure for a period of time;
   wherein the process for covering the container with a closure includes
      changing a position of the first side component with respect to the second side component;
   wherein the process for keeping the container covered with the closure for a period of time includes:
      pressing the first side component in a first direction against at least a first part of the first sidewall by at least the first elastic component attached to the first side component, the first side component being in direct contact with at least the first part of the first sidewall; and
      pressing the second side component in a second direction against at least a second part of the second sidewall by at least the second elastic component attached to the second side component, the second side component being in direct contact with at least the second part of the second sidewall.

2. The method of claim 1 wherein the process for covering the container with a closure includes placing the first top component between the one or more reservoirs and the second top component.

3. The method of claim 1 wherein the process for storing one or more fluid samples in one or more reservoirs of a container comprises using the container including the first sidewall and the second sidewall, the first sidewall and the second sidewall being concentric.

4. The method of claim 1 wherein the first direction and the second direction are at least 90 degrees apart.

5. The method of claim 4 wherein the first direction and the second direction are approximately opposite to each other.

6. A method for storing one or more fluid samples, the method comprising:
   storing one or more fluid samples in one or more reservoirs of a container, the container including a first sidewall and a second sidewall;
   covering the container with a closure, the closure including a first closure component and a second closure component, the first closure component including a first top component, a first side component and a first elastic component attached to the first side component, the second closure component including a second top component, a second side component and a second elastic component attached to the second side component, the first top component and the second top component being in different positions; and
   keeping the container covered with the closure for a period of time;
   wherein the process for keeping the container covered with the closure for a period of time includes allowing at least an exchange of vapor between the inside of the container and the outside of the container, the container being covered by the closure;
   wherein the process for covering the container with a closure includes changing a position of the first side component with respect to the second side component.

7. The method of claim 6 wherein the process for covering the container with a closure includes placing the first top component between the one or more reservoirs and the second top component.

8. The method of claim 6 wherein the process for storing one or more fluid samples in one or more reservoirs of a container comprises:
   surrounding the one or more fluid samples by the first sidewall; and
   surrounding the one or more fluid samples by the second sidewall, the second sidewall surrounding the first sidewall.

9. The method of claim 8 wherein the process for storing one or more fluid samples in one or more reservoirs of a container further comprises using the container including the first sidewall and the second sidewall, the first sidewall and the second sidewall being concentric.

* * * * *